US006830551B1

(12) United States Patent
Uchigaki et al.

(10) Patent No.: US 6,830,551 B1
(45) Date of Patent: Dec. 14, 2004

(54) BODY FLUID MEASURING INSTRUMENT AND BODY FLUID SAMPLER THEREOF

(75) Inventors: Takatoshi Uchigaki, Kyoto (JP); Kohei Ishida, Kyoto (JP); Shiro Matsuoka, Hyogo (JP)

(73) Assignee: Arkray, Inc., Kyoto (JP)

( * ) Notice: Subject to any disclaimer, the term of this patent is extended or adjusted under 35 U.S.C. 154(b) by 69 days.

(21) Appl. No.: 10/129,155

(22) PCT Filed: Nov. 8, 2000

(86) PCT No.: PCT/JP00/07865

§ 371 (c)(1),
(2), (4) Date: Jul. 22, 2002

(87) PCT Pub. No.: WO01/34029

PCT Pub. Date: May 17, 2001

(30) Foreign Application Priority Data

Nov. 8, 1999 (JP) .......................................... 11-316652

(51) Int. Cl.[7] ................................................ A61B 5/00
(52) U.S. Cl. ...................... 600/584; 600/347; 600/372; 606/181; 204/403.01
(58) Field of Search ............................... 600/309, 347, 600/365, 372, 373, 573, 576, 583, 584; 606/181, 182; 204/193, 403.01, 403.02, 403.04, 403.1, 403.11, 403.12

(56) References Cited

U.S. PATENT DOCUMENTS

| 5,165,407 A | * | 11/1992 | Wilson et al. ............... 600/345 |
| 6,051,392 A | * | 4/2000 | Ikeda et al. .................... 435/25 |
| 6,104,940 A | * | 8/2000 | Watanabe et al. ........... 600/345 |
| 6,275,717 B1 | * | 8/2001 | Gross et al. ................. 600/345 |
| 6,332,871 B1 | * | 12/2001 | Douglas et al. ............. 600/583 |

FOREIGN PATENT DOCUMENTS

| EP | 0199484 | 3/1993 |
| JP | 04-357452 | 12/1992 |
| JP | 05-203608 | 8/1993 |
| JP | 09-089885 | 4/1997 |
| JP | 09-094231 | 4/1997 |
| JP | 09-266898 | 10/1997 |
| JP | 09-285459 | 11/1997 |
| JP | 10-028683 | 2/1998 |

* cited by examiner

*Primary Examiner*—Charles Marmor
(74) *Attorney, Agent, or Firm*—Merchant & Gould P.C.

(57) ABSTRACT

A body fluid measuring apparatus includes a main body (20) and a body fluid sampler (30) attached to the main body (20). The body fluid sampler (30) includes a fixed member (35) fixed to the main body (20) and a movable member guided by the fixed member (35). The fixed member (35) is provided with a body fluid-sucking chamber (39) open at the tip of the fixed member (35) and a through-hole communicating therewith. The movable member (31) includes a lancet (32) acting as a first electrode and is reciprocatively movable for bringing the tip of the lancet (32) into and out of the tip of the fixed member (35). The body fluid-sucking chamber (39) is provided with a second electrode (36) and a reactive layer containing a reactive reagent necessary for measurement. The main body (20) includes an electronic circuit (24) for determining a measured value on the basis of an electrical signal from the lancet (32) as the first electrode and a second electrode. The main body also includes a drive mechanism (43) which drives the movable member for causing the tip of the lancet to project from the tip of the fixed member.

18 Claims, 8 Drawing Sheets

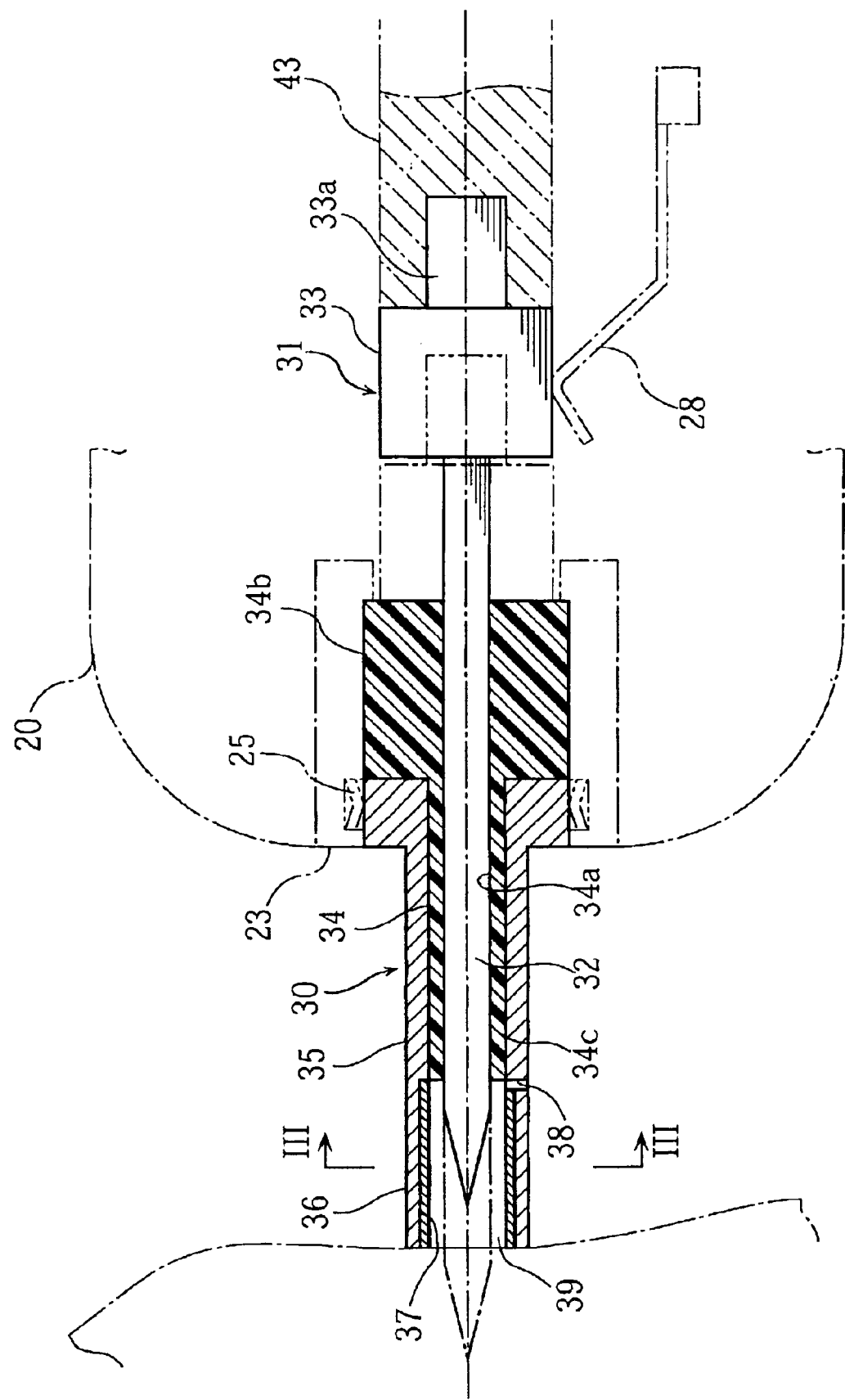

y=0.0567x+6.833
R²=0.9752

| Glucose Level/mg/dL | 800mV |
|---|---|
| 100 | 11.41 |
| 100 | 11.00 |
| 100 | 11.94 |
| 100 | 12.61 |
| 200 | 18.83 |
| 200 | 17.48 |
| 200 | 19.93 |
| 200 | 20.50 |
| 500 | 37.12 |
| 500 | 32.68 |
| 500 | 34.71 |

BODY FLUID MEASURING INSTRUMENT AND BODY FLUID SAMPLER THEREOF

TECHNICAL FIELD

The present invention relates to a body fluid measuring apparatus for measuring the concentration of a specific component contained in body fluid such as glucose contained in blood, and to a body fluid sampler for the apparatus.

BACKGROUND ART

For diabetes treatment, it is necessary to maintain, in a normal range, the concentration of glucose (hereinafter "blood glucose level") contained in the blood of a diabetes patient. An important treatment is the blood glucose level management by the patient. Particularly for treatment of insulin-dependent diabetes, the patient should inject insulin to keep the blood glucose level in a normal range. Therefore, measurement of the blood glucose level is essential for the patient.

A portable apparatus usable by a diabetes patient by himself or herself for measuring the blood glucose level is commercially available. For example, JP-B-8-20412 discloses such a blood glucose level measuring apparatus. The blood glucose level measuring apparatus comprises a main unit and a disposable test piece to be mounted on the main unit. An enzyme electrode is formed on the test piece. With this measuring apparatus, when the tip of the test piece contacts blood, a portion of the blood is sucked in by a reacting portion of the test piece by capillary phenomenon to cause an enzyme reaction and an electrochemical reaction in the reacting portion. As a result, an anode current flows to the electrode of the test piece. The anode current is converted to a blood glucose level in an arithmetic circuit in the main unit of the apparatus, and the result is represented on a display.

In order to bring an analyte such as blood into contact with a test piece in the measuring apparatus, a tool named "lancet" is commonly used, as disclosed in JPA-9-266898 for example. The lancet is a tool used for making a small hole or cut in the skin of a finger tip, for example, of a patient. Upon bleeding from the hole or cut, blood is brought into contact with a predetermined site of the test piece for further supply of blood used for measurement of the blood glucose level.

However, with the conventional common self-measurement of the blood glucose level, the lancet for sampling blood is separate from the measuring apparatus, so that the two tools need to be carried by the patient. Moreover, it is necessary to separately perform the steps of injuring the skin with the lancet and of bringing the bleeding blood into contact with the test piece, thus making measurement still complex. In particular, when bringing the blood into contact with the test piece, since a predetermined amount of blood needs to be brought into contact with a predetermined portion of the test piece, it is difficult for an untrained or weak-sighted patient to perform this step quickly and properly.

In addition, the above-described conventional blood glucose level measuring apparatus is designed to suck blood from a hole at the tip of the test piece onto a planar enzyme electrode in the reacting portion by capillary phenomenon. Therefore, at least 3 to 5 $\mu l$ of blood needs to be brought into contact with the test piece to ensure that a necessary amount of blood reaches the reacting portion. If the amount of blood is insufficient or if a sufficient amount of blood is not deposited appropriately on a small area surrounding the tip hole of the test piece, the apparatus may suffer erroneous measurements. In particular, such a case is more likely to occur with respect to patients such as infants and the elderly who tend to suffer insufficient bleeding of blood from a cut.

JP-A-9-94231, JP-2616331, and JP-A-9-89885 disclose a measuring apparatus which comprises a lancet and an enzyme electrode for providing the dual functions of blood extraction and measurement.

However, use of the apparatus of JP-A-9-94231 requires the sucking of blood by piercing the skin with a needle-like lancet during blood glucose level measurement, which causes continual pain. Further, since disposability of the blood sampling unit is not intended, problems therefore arise with regard to hygienic management and utility for repeated use. The apparatus of JP-2616331 also necessitates the sucking of blood with a needle-like lancet held stabbed into the skin and disposability of the blood sampling unit is not intended. On the other band, the apparatus of JP-A-9-8985 is designed to instantaneously complete a skin injuring operation with a lancet However, this apparatus is equipped with two pairs of electrodes in addition to the lancet and thereby a process for manufacturing the apparatus becomes complex with a resultant increase of the manufacturing cost. Moreover, with this apparatus, no ideas have been put forward concerning alleviation of pain in blood sampling by reducing the amount of blood for measurement.

DISCLOSURE OF THE INVENTION

An object of the present invention is to eliminate or relieve the above described problems. Specifically, the object of the present invention is to simplify the patient's action needed for measurement. A further object of the present invention is to provide a body fluid measuring apparatus and a body fluid sampler therefor, which require a significantly decreased amount of analyte for measurement with a high reliability to thereby relieve the pain attendant therewith.

According to a first aspect of the present invention, there is provided a body fluid measuring apparatus comprising a main body and a body fluid sampler fitted to the main body. The body fluid sampler comprises a fixed member fixed to the main body and a movable member guided by the fixed member. The fixed member is formed with a body fluid-sucking chamber open at a tip of the fixed member and a through-hole communicating therewith. The movable member comprises a lancet acting as a first electrode and is reciprocatively movable for bringing the tip of the lancet into and out of the tip of the fixed member. The body fluid-sucking chamber is provided with a second electrode and a reactive layer containing a reactive reagent necessary for measurement. The main body comprises an electronic circuit for providing a measurement on the basis of an electrical signal from the lancet as the first electrode and a second electrode, and a drive mechanism for driving the movable member for causing the tip of the lancet to project from the tip of the fixed member.

Preferably, the fixed member comprises a cylindrical electrode acting as the second electrode and an insulator for electrically separating the cylindrical electrode from the lancet. The cylindrical electrode and the lancet are concentrically arranged.

Preferably, a surface of the insulator facing the lancet is hydrophobically treated.

Preferably, the reactive layer is provided over an entire wall surface defining the fluid-sucking chamber in the cylindrical electrode.

Preferably, the drive mechanism comprises an automatic drive mechanism for driving the movable member to first cause the tip of the lancet to project from the tip of the fixed member and to subsequently cause the tip of the lancet to retreat from the tip of the fixed member.

Preferably, the main body has a fixed terminal connected to the electronic circuit, and the movable member of the body fluid sampler comprises a contact portion in slidable contact with the fixed terminal for electrically connecting the lancet to the fixed terminal.

Preferably, the main body has an annular spring terminal for electrically connecting the second electrode to the electronic circuit, and the fixed member of the body fluid sampler is detachably fixed to the main body under urging of the annular spring terminal.

Preferably, the fixed member is provided with an air-vent hole for enabling the fluid-sucking chamber to communicate with an external space.

Preferably, the inner diameter of the cylindrical electrode is 0.4–1.2 mm, and more preferably 0.5–0.8 mm.

Preferably, the tip of the lancet is pointed like a needle, and the outer diameter thereof is 0.2–0.4 mm.

Preferably, each of the first electrode and the second electrode is formed from carbon, a noble metal, or a composite of these materials.

In use of the body fluid measuring apparatus according to the first aspect of the present invention, the tip of the body fluid sampler mounted to the apparatus, i.e. the tip of the fixed member,is pressed against a finger tip, for example, of a patient, the movable member is driven forward by operation of the drive mechanism of the main body to injure the skin of the patient finger tip with the lancet tip of the movable member projecting beyond the tip of the fixed member. Preferably, the movable member is subsequently moved backward for a predetermined distance, but the lancet tip still remains in the fluid-sucking chamber even in this retreated state. While holding the tip of the fixed member pressed against the finger tip for some time, blood bleeding from the injury is sucked into the fluid-sucking chamber by the capillary phenomenon. The sucked blood dissolves the reactive layer provided in the fluid-sucking chamber and contacts the electrode (operative electrode for example) mounted on the fixed member in exposure to the fluid-sucking chamber as well as the lancet as the electrode (counterpart electrode, for example). The reactive layer contains, for blood glucose level measurement, a reactive reagent such as glucose oxidase which is an oxidization enzyme, and potassium ferricyanide as a mediator.

When the reactive layer is dissolved in blood, an enzyme reaction starts, as represented by the following formula (1) As a result, potassium ferricyanide contained in the reactive layer is reduced to cumulatively produce potassium ferrocyanide which is a reduced-type electron carrier. The amount of potassium ferrocyanide is proportional to the concentration of the substrate, i.e., the glucose level of the blood. The reduced-type electron carrier produced in a predetermined time is electrochemically oxidized as represented by the following formula (2), thereby generating an anode current. The electronic circuit in the main body of the measuring apparatus performs calculation to determine the glucose level (blood glucose level) based on the detected anode current. Preferably, the result of measurement is displayed on a display mounted on a surface of the main body.

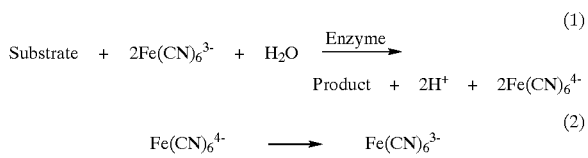

In this way, with the body fluid measuring apparatus according to the first aspect, it is possible to perform body fluid measurement such as blood glucose level measurement easily and properly only by causing the lancet to project from the tip of the fixed member while keeping the tip of the body fluid sampler in the main body pressed against the finger tip of the patient. The process required for using the body fluid measuring apparatus according to the present invention is much simpler than the conventional measuring process which requires the steps of injuring the skin with a lancet and bringing the bleeding blood into contact with a test piece on a measuring apparatus.

Moreover, in the case of an electrode structure wherein the electrode of the fixed body is cylindrical to accommodate therein the lancet as a counterpart electrode, the amount of body fluid necessary for measurement can be reduced. For example, assuming that the cylindrical electrode has an inner diameter of 0.6 mm and the fluid-sucking chamber has an axial length of 1 mm, the electrode area is 1.884 mm$^2$ and the fluid-sucking chamber has a volume of 0.2826 $\mu$l. Due to the lancet having a portion residing in the fluid-sucking chamber, the required volume of the analyte further decreases. In addition, the bleeding blood directly entering the fluid-sucking chamber from the skin need only flow a very short distance before reaching the two electrodes. This means that the amount of analyte required by the body fluid measuring apparatus according to the present invention is smaller than the volume corresponding to the fluid-sucking chamber. Considering that the conventional measuring apparatus mentioned in the BACKGROUND ART portion requires 3–5 $\mu$l of analyte, it can be understood how small the amount of analyte required by the electrode structure according to the present invention is. The smaller the required amount of sample is, the higher is the reliability of measurement and the lower is the pain.

According to a second aspect of the present invention, another body fluid measuring apparatus is provided which comprises a main body and a body fluid sampler fitted to the main body. The body fluid sampler comprises a fixed member fixed to the main body and a movable member guided by the fixed member. The fixed member is formed with a through-hole. The movable member comprises a lancet and is reciprocatively movable for bringing the tip of the lancet into and out of the tip of the fixed member. The lancet comprises a tube, an axial core inserted therein, and an insulator for electrically separating the tube and the core. The tube serves as a first electrode, whereas the axial core serves as a second electrode. The tip of the lancet is provided with a reactive reagent for measurement. The main body comprises an electronic circuit for providing a measurement on the basis of an electrical signal from the tube and the axial core, and a drive mechanism which drives the movable member for causing the tip of the lancet to project from the tip of the fixed member.

Preferably, the tube projects further tipwise than the axial core and the insulator, and the reactive reagent is attached to the tip of the axial core.

Preferably, the drive mechanism comprises an automatic drive mechanism for driving the movable member to first cause the tip of the lancet to project from the tip of the fixed member and to subsequently cause the tip of the lancet to retreat from the tip of the fixed member.

Preferably, the main body has a first and a second fixed terminals connected to the electronic circuit. Further, the movable member comprises a first contact portion in slidable contact with the first fixed terminal for electrically connecting the tube to the first fixed terminal and a second contact portion in slidable contact with the second fixed terminal for electrically connecting the axial core to the second fixed terminal.

Preferably, the fixed member is provided with an air-vent hole for enabling fluid-sucking chamber to communicate with an external space.

The body fluid measuring apparatus according to the second aspect of the present invention functions mechanically, chemically, and electrically in substantially the same way as the apparatus according to the first aspect. Blood bleeding from the injury is sucked by the tip of the lancet by the capillary phenomenon. While dissolving the reactive reagent attached to the tip of the axial core, the sucked blood contacts the axial core of the lancet (operative electrode for example) as one electrode and the tube of the lancet as the other electrode (counterpart electrode for example.) Thereafter, the anode current is measured by the electronic circuit inside the main body.

As in the preferred embodiment, if the tube of the lancet projects further tipwise than the axial core and the insulator to form a very small space at the tip of the lancet with the reactive reagent attached to the tip of the axial core, blood entering the small space reliably contacts both the axial core and the tube as electrodes. As a result, a very small amount of blood gives rise to a current sufficient for measurement.

Consequently, the body fluid measuring apparatus according to the second aspect provides the same advantages as that according to the first aspect. Furthermore, the blood amount to be sampled may be an amount needed only for contact with the two kinds of electrodes formed at the tip of a very thin lancet and thus, the tip of the lancet need only pierce the skin to a smaller depth than is necessary for the apparatus according to the first aspect. This contributes to additional relief of the pain while also improving reliability of measurement.

A third aspect of the present invention provides a body fluid sampler mounted, in use, on a body fluid measuring apparatus. The body fluid sampler comprises a fixed member and a movable member guided by the fixed member. The fixed member is formed with a body fluid-sucking chamber open at a tip of the fixed member and a through-hole communicating therewith. The movable member comprises a lancet acting as a first electrode and is reciprocatively movable for bringing the tip of the lancet into and out of the tip of the fixed member. The body fluid-sucking chamber is provided with a second electrode and a reactive layer containing a reactive reagent necessary for measurement.

Preferably, the movable member comprises a contact portion for slidable contact with a fixed terminal mounted to a main body of the body fluid measuring apparatus to which the body fluid sampler is attached, and the contact portion is held in conduction with the lancet.

The body fluid sampler according to the third aspect of the present invention is used as one for the apparatus according to the first aspect. Therefore, the body fluid sampler according to the third aspect of the present invention has the same advantages as those described concerning the first aspect.

According to the fourth aspect of the present invention, another body fluid sampler is provided which is mounted, in use, on a body fluid measuring apparatus. The body fluid sampler comprises a fixed member and a movable member guided by the fixed member. The fixed member is formed with a through-hole. The movable member comprises a lancet and is reciprocatively movable for bringing the tip of the lancet into and out of the tip of the fixed member. The lancet comprises a tube, an axial core inserted therein, and an insulator for electrically separating the tube and the core. The tube serves as a first electrode, whereas the axial core serves as a second electrode. The tip of the lancet is provided with a reactive reagent for measurement.

Preferably, the movable member comprises a first contact portion for slidable contact with a first fixed terminal mounted to a main body of the body fluid measuring apparatus to which the body fluid sampler is attached, and the first contact portion is held in conduction with the tube. The movable member also comprises a second contact portion for slidable contact with a second fixed terminal mounted to the main body, and the second contact portion is held in conduction with the axial core.

The body fluid sampler according to the fourth aspect of the present invention is used as one for the apparatus according to the second aspect. Therefore, the body fluid sampler according to the fourth aspect of the present invention has the same advantages as those described concerning the second aspect.

Other features and advantages of the present invention will become clear from the detailed description presented below with reference to the drawings.

BRIEF DESCRIPTION OF THE DRAWINGS

FIG. 2 is an enlarged longitudinal section view showing a body fluid sampler of the body fluid measuring apparatus according to the first embodiment of the present invention.

THE BEST MODE FOR CARRYING OUT THE INVENTION

Figure 1:
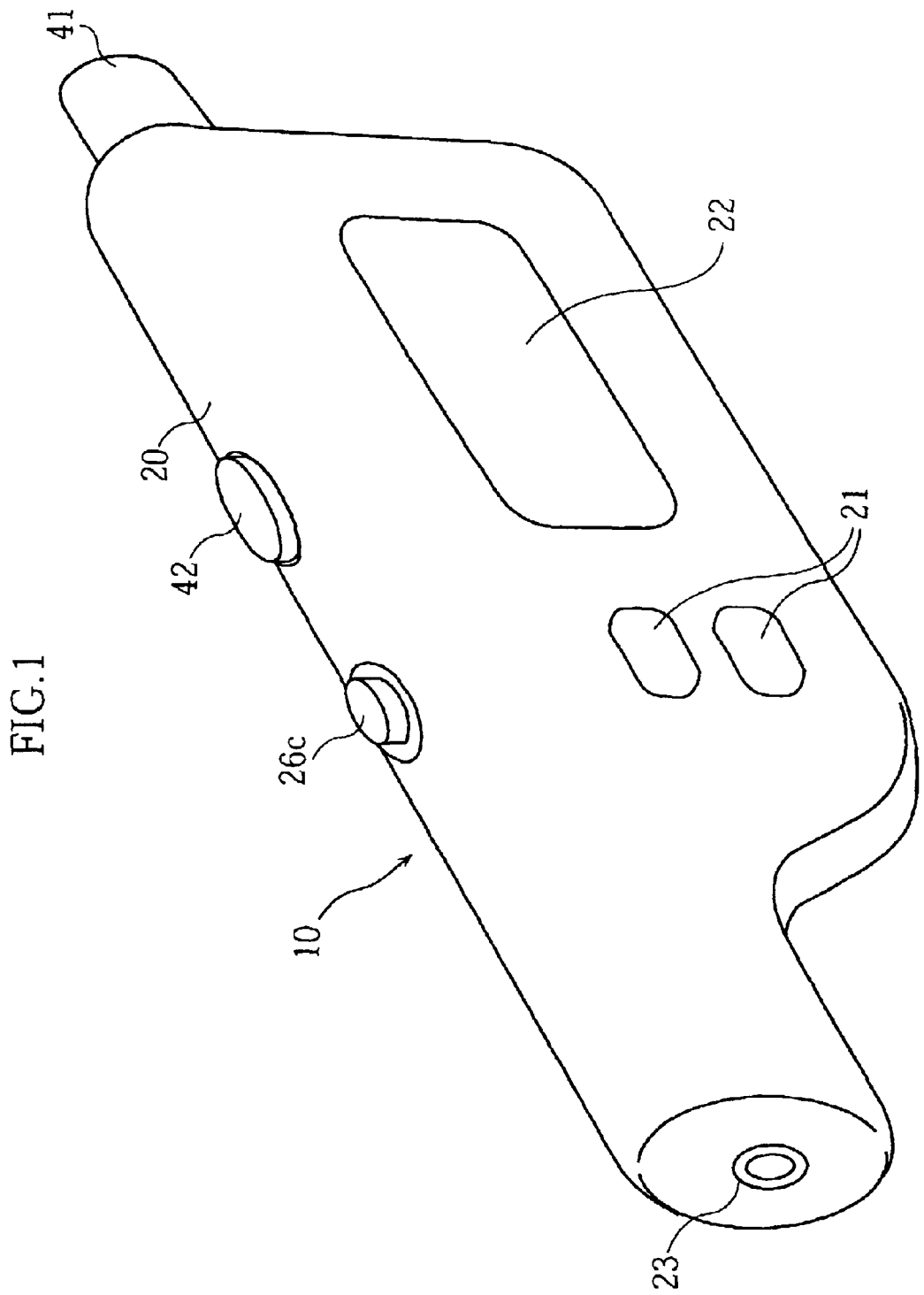
FIG. 1 is perspective view showing a main body of a body fluid measuring apparatus according to the present invention.
Figure 4:
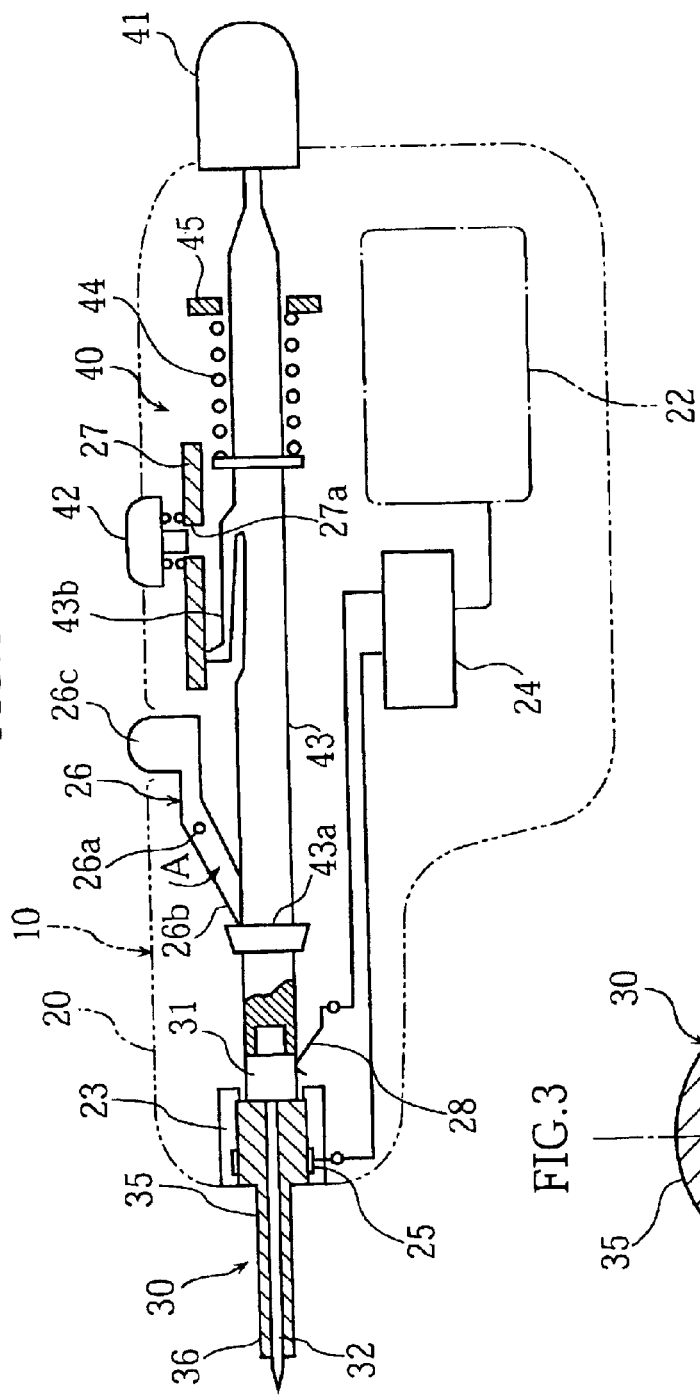
FIG. 4 is a partially sectional schematic figure showing the appearance of an internal structure of the body fluid measuring apparatus according to the first embodiment of the present invention.
Figure 5:
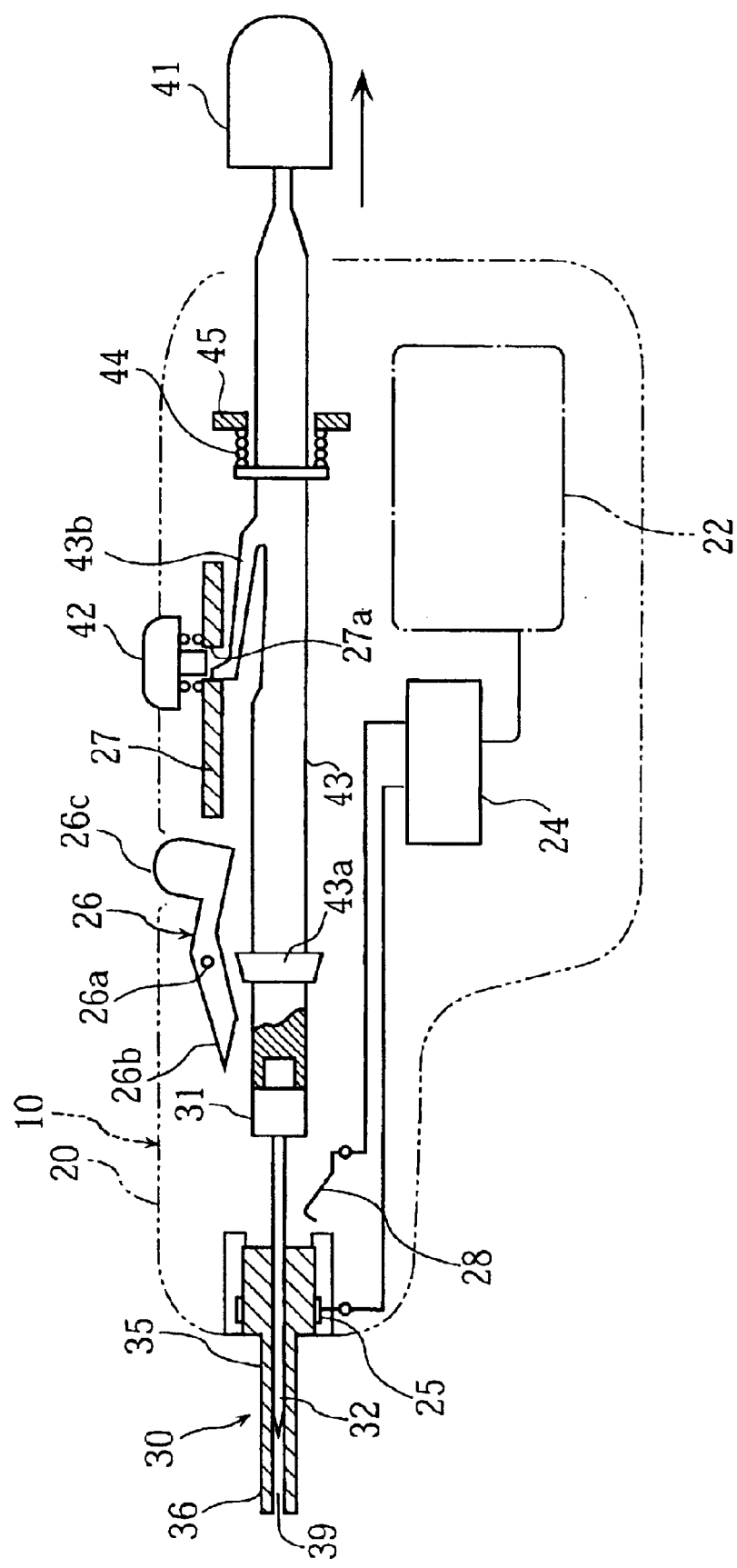
FIG. 5 is the partially sectional schematic figure showing another appearance of the internal structure of the body fluid measuring apparatus according to the first embodiment of the present invention.
Figure 6:
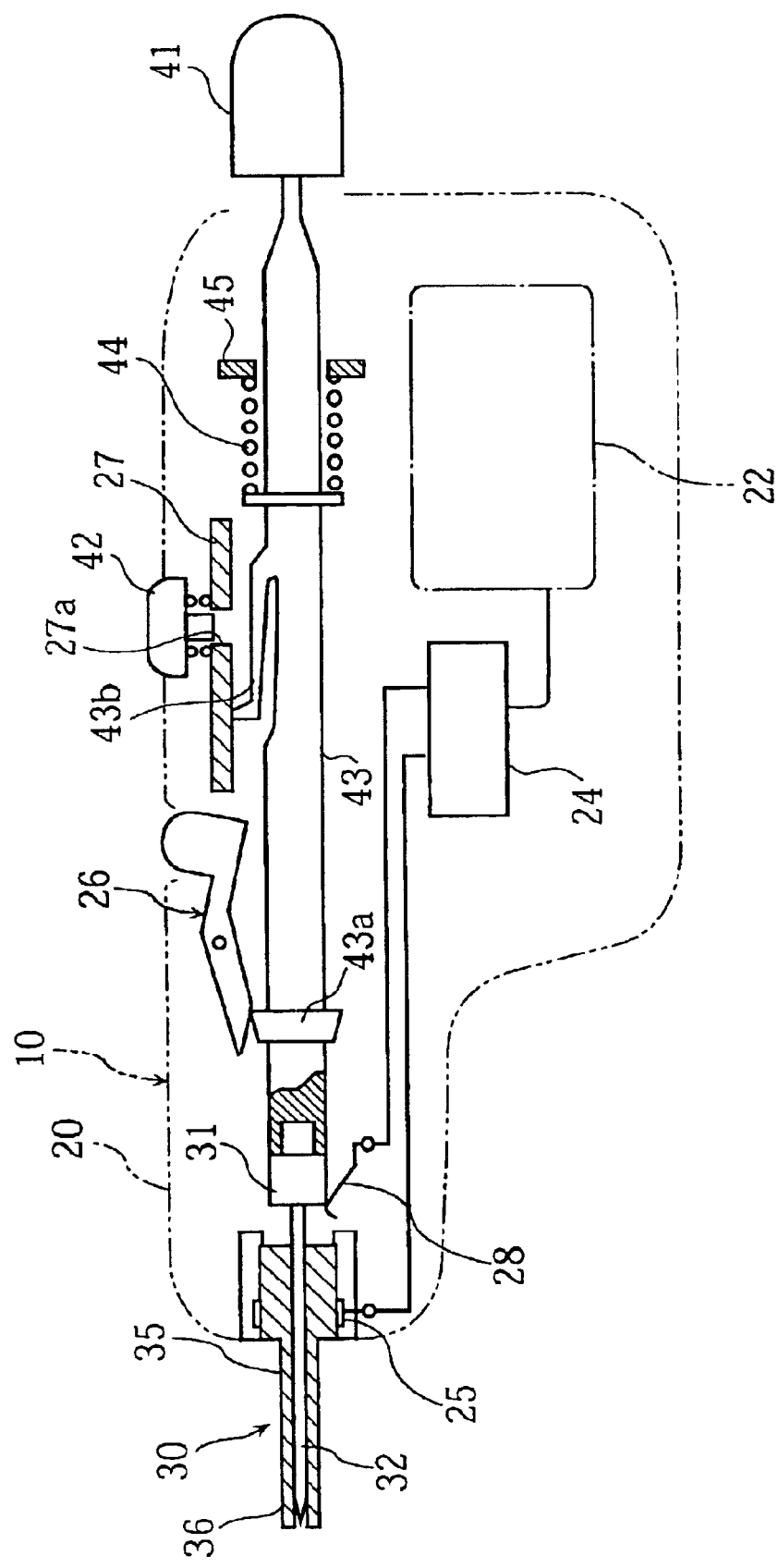
FIG. 6 is the partially sectional schematic figure showing another appearance of the internal structure of the body fluid measuring apparatus according to the first embodiment of the present invention.

The preferred embodiment of the present invention will be described with reference to the drawings. FIGS. 1 to 6 show a first embodiment of the present invention. The body fluid measuring apparatus 10 according to the present invention comprises a main body 20 and a body fluid sampler 30. As shown in FIG. 1, a switch button 21, a display 22, a release switch 26c and an ejection button 42 are provided on the surface of the main body 10. A socket 23 for housing the body fluid sampler 30 is formed at the front end (on the left of the figure) of the main body 10 and a knob 41 is fitted to a rear end (on the right side of the figure) of the main body 10. A drive mechanism 40 for driving the movable member 31 installed in the body fluid sampler 30 described later is housed in the main body 10, and an electronic circuit 24 containing a microcomputer is also built-in, as shown in FIGS. 4 to 6. The above described knob 41 constitutes part of the drive mechanism 40.

Figure 3:
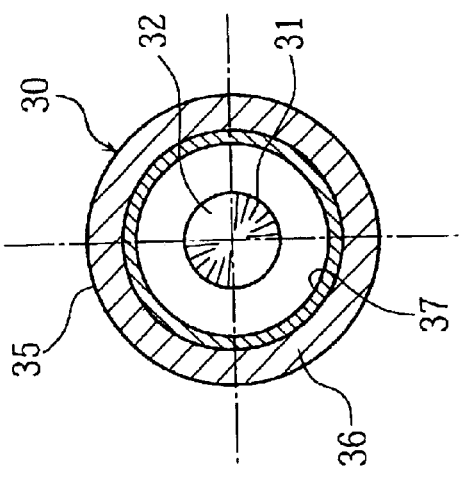
FIG. 3 is a enlarged longitudinal section view along a line III—III of the body fluid sampler shown in FIG. 2.

FIG. 2 is an enlarged longitudinal sectional view showing the body fluid sampler 30 and an adjacent area of the body fluid measuring apparatus 10 according to the first embodiment of the present invention. An imaginary line represents a part of an external form of the main body 20 and the skin making contact with the tip of the body fluid sampler 30. FIG. 3 is an enlarged longitudinal section view along the line III-III of the body fluid sampler shown in FIG. 2. As shown in FIG. 2, the body fluid sampler 30 is used by mounting on the socket 23 of the main body 10. The body fluid sampler 30 has a cylindrical fixed member 35 fixed to the socket 23 and a movable member 31 capable of proceeding and retreating in an axial direction within the fixed member 35.

The cylindrical fixed member 35 has an insulator 34 made from a resin and a cylindrical electrode 36.

The insulator 34, in which the through-hole 34a is formed, has a large diameter part 34b and a small diameter part 34c. The cylindrical electrode 36 is fitted to an outside surface of the small diameter part 34c of the insulator 34 and a full length thereof is larger than the length of the small diameter part 34c of the insulator 34 in the axial direction. In other words, the cylindrical electrode 36 projects to the front of the small diameter part 34c of the insulator 34. The cylindrical electrode 36 is a carbon electrode containing carbon, for example, as a main component. The cylindrical electrode 36 may be formed as a noble metal electrode such as platinum and gold or a composite electrode made of carbon and the noble metal.

The movable member 31 comprises a larger diameter part 33 formed integrally on a base of a lancet 32, and the lancet 32. The lancet 32 has an external diameter corresponding to the through-hole 34a of the insulator 34 and the tip thereof is formed in a tapered tip shape. The movable member 31 is, in the state where the lancet 32 is passed through the through-hole 34a of the insulator 34, constituted to be reciprocatively movable with respect to the fixed member 35 in the axial direction in a predetermined distance. The wall face of the through-hole 34a is hydrophobically treated and thus the sample, i.e. blood, can be appropriately prevented from entering an area between the insulator 34 and the lancet 32. According to the present invention, the lancet 32 does not just act as a blade but also acts as an electrode as described later. Therefore, the entire movable member 31 is formed from a conductive material such as stainless steel.

The reactive layer 37 containing the reactive reagent necessary for measurement is formed on an inner face of the part projecting to the front of the small diameter part 34c of the insulator 34 of the cylindrical electrode 36. In the case where the body fluid measuring apparatus 10 according to the present invention is constituted as the blood glucose level measuring apparatus, the reactive layer 37 contains glucose (GOD) oxidase as the oxidizing enzyme and potassium ferricyanide or ferrocene. The reactive layer 37 can be prepared by dipping the cylindrical carbon electrode 36 in a aqueous solution of GOD and potassium ferricyanide, for example, and removing the aqueous solution attached to an outer surface of the electrode 36 by wiping followed by drying. In order to improve the extent to which the reactive layer is deposited on the cylindrical electrode 36 and hydrophilicity with respect to the sample, before dipping the electrode 36 in the aqueous solution, it is preferable to form a hydrophilic high polymer layer such as carboxymethyl cellulose on the electrode 36 in advance and blend the same hydrophilic high polymer with the mixture aqueous solution. An air-vent 38 is formed in the vicinity of a boundary area of the reactive layer 37 and the insulator 34 of the cylindrical electrode 36, so as to pass through a body fluid-sucking chamber 39 defined by the cylindrical electrode 36 and to the outside. As mentioned later, the air-vent hole 38 is prepared to enhance sucking of the sample into the body fluid-sucking chamber 39 by the capillary phenomenon.

The size of the cylindrical electrode 36 and the lancet 32 is not specially restricted. However, as exemplified below, setting is possible to make the necessary sample very small in comparison with the conventional sample amount. In order to properly suck the sample into the cylindrical electrode 36, i. e. the body fluid-sucking chamber 39, by the capillary phenomenon, in the case where the lancet 32 has an external shape with 0.3 mm length, for example, almost equal to that of a lancet needle, the cylindrical electrode 36 is preferably designed to have an inner diameter of 0.6 mm, for example, defining a blood-sucking space with a length of 1 mm, for example, in the axial direction. In consideration of easy preparation of the lancet 32 and the cylindrical electrode 36 and occurrence of a preferable capillary phenomenon, it is preferable to select the outer diameter of the lancet 32 in a range from 0.2 mm to 0.4 mm, for example, and to select the inner diameter of the enzyme electrode in the range from 0.4 to 1.2 mm, preferably 0.5 mm to 0.8 mm.

It is preferable for the body fluid sampler 30 to be disposable from a measurement and hygiene point of view, with a new body fluid sampler 30 being used for each measurement.

As shown in FIG. 2, the socket 23 is basically constituted to allow insertion of the base of the fixed member 35 into the body fluid sampler 30. The socket 23 has a terminal 25 coming into contact with the base of the cylindrical electrode 36 of the fixed member 35 when the body fluid sampler 30 is inserted therein. The terminal 25 is mounted to electrically connect the cylindrical electrode 36 to the electronic circuit 24 inside the main body. The terminal 25 is, as shown in FIG. 2, the annular spring terminal having a V-shape section. The fixed member 35 is detachably fixed to the main body by energizing the spring of the terminal 25. Specifically, when the body fluid sampler 30 is inserted into the socket 23, the terminal 25 becomes flat to widen an angle of a top of the V shape and presses the base of the fixed body 35. Though not illustrated in any figure, a notch may be prepared in a location corresponding to the top of the V shape of the terminal 25 in the cylindrical electrode 36.

FIGS. 4 to 6 are partially sectional schematic figures showing the appearance of the internal structure of the body fluid measuring apparatus 10. Inside the main body 20, the drive unit 43, in which a projection 33a projecting from the larger diameter part 33 of the movable member 31 when the body fluid sampler 30 is inserted into the socket 23, is housed, is incorporated movably in the axial direction of the body fluid sampler 30. To a rear end of the drive unit 43, the knob 41 is connected to project from the rear end of the main body 20. Consequently, when the knob 41 in the rear end is held and pulled backwards, the drive unit 43 moves backwards in the axial direction. A coil spring 44 is arranged along the drive unit 43 to allow an energizing force to act in a forward direction against the drive unit 43 when the drive unit 43 moves backwards. In the case of the present embodiment, one end of the coil spring 44 is connected to the drive unit 43 and the other end is connected to a supporting plate 45 fixed to the main body 10. Therefore, the coil spring 44 contributes to not only energizing the drive unit 43 forward in a retreating position thereof, but also once the drive unit 43 moves to a front end of a moving range (that is, a state where the front end of the lancet 32 projects from the front end of the body fluid sampler 30 to a predetermined length), the energizing of the coil spring 44 acts in a backward direction and the drive unit 43 is pulled back a predetermined distance to return to the original state.

A stopper lever 26 is supported inside the main body 20. The stopper lever 26 is capable of rocking around a shaft 26a, with a stopper hook 26b formed on one end and a release button 26c exposed to the outside of the main body 20 formed on the other end. A reset button, not illustrated, allows this stopper lever 26 to take on a reset state when turned in a direction indicated by an arrow A shown in FIG. 4. In the reset state, this stopper lever 26 stops backward motion of the drive unit 43 by engagement of the stopper hook 26b with a step 43a of the drive unit 43. However, when the release button 26c is pressed, engagement of the stopper hook 26b with the step 43a is released to make the backward motion of the drive unit 43 possible. The stopper hook 26b extends tilting against the drive unit 43 to approach the drive unit 43 toward a forward position overall and is capable of being turned back around with the shaft 26a as a fulcrum, and thus does not inhibit a forward ejecting action of the drive unit 43 mentioned later.

A latch lever 43b is formed at a predetermined location in the axial direction of the drive unit 43. This latch lever 43b is subjected to elastic deformation by being pressed by the plate member 27 fixed to the main body 20 in almost all processes of the drive unit 43, but at a predetermined position of the drive unit 43, elastic deformation is eliminated to allow engagement with an engaging hole 27a formed in the main body as shown in FIG. 5. Engagement of the latch lever 43b with the engaging hole 27a makes it possible to maintain the state where the drive unit 43 is pulled backwards by receiving the energizing force from the spring 44 to a forward position. The ejection button 42 is formed at a position corresponding to the position of the engaging hole 27a so as to be exposed from the top of the main body 20. When this ejection button 42 is pressed, engagement of the latch lever 43b with the engaging hole 27a is forcedly released.

As described above, the drive unit 43, the coil spring 44, and the ejection button 42 collaborate to constitute the drive mechanism 40 to drive the movable member 31 and the lancet 32 of the body fluid sampler 30 forward vigorously.

Moreover, the lancet 32, acting as the electrode in the body fluid sampler 30, and the fixed terminal 28 for making contact with the movable member 31, are mounted inside the main body 20. The terminal 28 is formed so as to be capable of making sliding contact with the larger diameter part 33 in order to make conductive contact with the larger diameter part 33 of the movable member 31, when the movable member 31 is in a predetermined position in the axial direction.

In the socket 23, the terminal 25 for making contact with the cylindrical electrode 36 and the terminal 28 for making contact with the lancet 32 as the counterpart electrode and the movable member 31 are connected to the electronic circuit 24. This electronic circuit 24 comprises a microcomputer and other components, determines a measuring value such as the blood glucose level of the matter to be detected from the anode current appearing as a result of reaction with oxygen and electrochemical reactions by using a calibration curve as described later, and has a function for displaying the results of measurements on the display 22 arranged on the surface of the main body 20.

According to the above described body fluid measuring apparatus 10, the blood glucose level can be measured as follows. Before measurement, at first, as shown in FIG. 4, the body fluid sampler 30 must be inserted into the socket 23 of the main body 20. For insertion of the body fluid sampler 30, before insertion, the drive unit 43 is positioned in front of a moving path thereof and the backward motion of the drive unit 43 is stopped by the stop lever 26. Specifically, the knob 41 is pressed to position the drive unit 43 in a position in front of the movement path and then, the stop lever 26 is turned in the direction of the arrow A by the reset button, not illustrated, to engage the stopper hook 26b with the step 43a of the drive unit 43. In this state, when the body fluid sampler 30 is inserted into the socket 23, as shown in FIG. 4, a base end of the movable member 31 of the body fluid sampler 30 is received and held by the front end of the drive unit 43.

Then, the release button 26c of the stop lever 26 is pressed down to make the backward motion of the drive unit 43 possible. Also, the knob 41 is pulled and, at the point where the drive unit 43 and the movable member 31 and the lancet 32 connected thereto retreat by the predetermined distance, the latch lever 43b is automatically engaged with the engaging hole 27a of the plate member 27. As a result, as shown in FIG. 5, the spring 44 energizes the drive unit 43 to hold the retreating state.

Next, the ejection button 42 is pressed down while pressing the tip of the body fluid sampler 30, i.e. the tip of the cylindrical electrode 36 on the finger tip of the patient. Depressing the ejection button 42 allows release of the engagement of the latch lever 43b and the drive unit 43, the movable member 31 and the lancet 32 are forcibly ejected for the predetermined distance forward by an elastic force generated by the spring 44. Then, as shown in FIG. 2 using the imaginary line, the tip of the lancet 32 projects from the tip of the cylindrical electrode 36 for an appropriate length resulting in injury of the skin of the patient. At the next instant, the lancet 32 is, as shown in FIG. 2 and FIG. 3, pulled back for the predetermined distance by a pull-back force created by the spring 44. Also after pull-back, it is better if the tip of the lancet 32 faces the space in the cylindrical electrode 36.

Blood bled from the injury produced by the lancet 32 is sucked into the body fluid-sucking chamber 39 defined by the cylindrical electrode 36 through a capillary phenomenon. Blood sucked in such a manner dissolves the reactive layer 37 formed on the inner wall of the electrode 36. As described above, when the reactive layer 37 is dissolved by blood, the enzyme reaction expressed by the formula (1) commences. As a result, potassium ferricyanide contained in the reactive layer 37 is reduced and potassium ferrocyanide being a reductive electron carrier is accumulated. The amount of potassium ferrocyanide is proportional to the substrate concentration, i. e. blood glucose level. When a predetermined voltage is applied to blood between electrodes, the reductive electron carriers accumulated in a specific period are oxidized by an electrochemical reaction as shown in the Formula (2) to cause the anodal current. The electronic circuit 24 in the main body 20 of the measuring apparatus performs calculation and determination of the glucose level (blood glucose level) based on the anode current measured. The result of measurement is displayed on the display 22 mounted on the surface of the main body. The result of measurement may be announced to a user through a speech output in place of or together with displaying on the display 22.

As described above, according to the body fluid measuring apparatus 10 of the present invention, the tip of the body fluid sampler 30 mounted on the main body 20 is kept pressed onto the finger tip of the patient in order to properly carry out a measurement for body fluid, such as the blood sugar level. The operation required for use of the body fluid measuring apparatus 10 is substantially simplified in comparison with the conventional measuring method, in which necessary operations are to injure the skin by using the lancet and to cause blood bled to come into contact with the test piece mounted on the measuring apparatus.

According to the present invention, the electrode structure adopted has one electrode being cylindrical and the lancet 32 as the counterpart electrode inside the cylindrical electrode, and therefore, the amount of body fluid required for measurement can be significantly reduced. As the result, it becomes possible to avoid the occurrence of a time lag in the current caused by an varying reaction rate that may arise for large samples, resulting in improvement of accuracy of the value measured.

According to the present invention, pain occurring at the time of measurement can be effectively relieved. If a size and a depth of the injury caused by the lancet is decreased as much as possible, the pain may be almost completely alleviated. However, the conventional apparatus requires blood of a certain amount or more due to the design of the blood sampler, and hence, alleviation of pain is insufficient However, according to the present invention, the lancet 32 and the cyindnical electrode 36 functioning as a pair of electrodes also function as members or defining the space 39 for sucking blood and therefore, the necessary blood amount can be directly and efficiently regulated. Consequently, through constituting the blood sampler 30 to make the blood amount sampled by the measuring apparatus a very small volume, the pain can be effectively alleviate.

Figure 7:
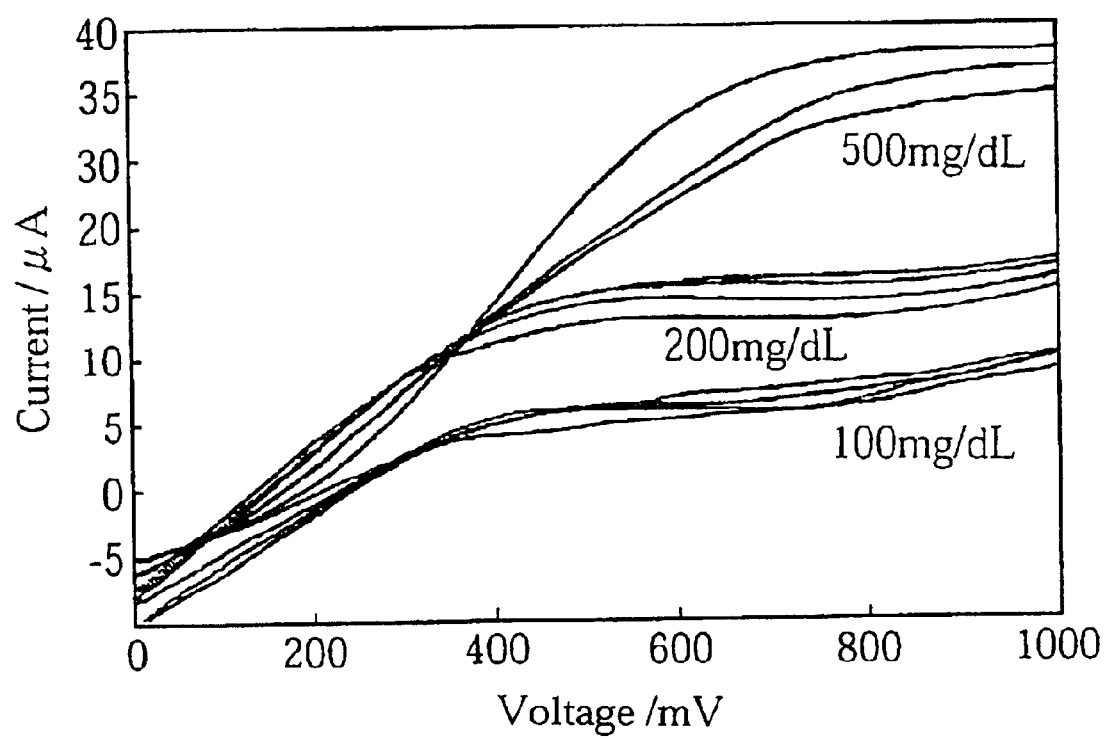
FIG. 7 is a figure illustrating a result of a measurement experiment using the body fluid measuring apparatus according to the first embodiment of the present invention.

FIG. 7 and FIG. 8 show the result of a measurement experiment employing the body fluid sampler with the above described shape. The cylindrical fixed body 35 used in this experiment has a 2 mm outer diameter, a 0.8 mm inner diameter, a 7 mm length in the axial direction, and the air-vent hole 38 at a position 2.5 mm away from the tip in the axial direction. The lancet 32 used in the movable member 31 has a 0.36 mm outer diameter, a 55 mm length (substantially effective length is 3 mm) and a region, which ranges from the base end side to a 2 mm length position, covered with a tube having a 0.8 mm outer diameter. Thus, the space defined by the cylindrical electrode 36 has a 0.8 mm inner diameter and at least a 2.5 mm length to keep a volume of 1.2566 $\mu$l. The fixed member 35 is ultrasonically cleansed in distilled water and then dipped in 2 $\mu$l of a mixed aqueous solution prepared by blending 0.25% by weight of carboxymethyl cellulose (CMC) with 20% by weight of isopropyl alcohol, and dried at 50° C. for about 15 minutes to finally form a hydrophilic high polymer layer as a first layer of the reactive layer 37. The fixed member 35 is dipped in 2.5 $\mu$l of the mixed aqueous solution prepared by blending 333 U/ml (U is a practical unit showing an efficacy of an enzyme and a hormone, for example, conforming to international standards) GOD and 26.7 mg/ml potassium ferricyanide, and then dried at 50° C. for about 10 minutes to further form a second layer on the first layer of the reactive layer 37. The reactive layer 37 is constituted by the first and the second layers.

For such a fixed member 35, the experiment was carried out by employing the body fluid sampler 30, in which the lancet 32 covered with the tube for insulation is inserted. The samples used for measurement were 0.9% by weight of an NaCl aqueous solution containing 100, 200, and 500 mg/dl glucose. This aqueous solution was sucked into the body fluid-sucking chamber 39 defined by the electrode 36 of the fixed member 35 through capillary phenomenon. As the method for measurement, the state, in which the NaCl aqueous solution is sucked in the space 39, is maintained for 15 seconds and then cyclic voltammetry is applied. As conditions for measurement, a sweep rate was 100 mV/sec and a sweep range was 0 to 1000 mV. The results of the measurement will be shown in FIG. 7.

Figures 8A, 8B:
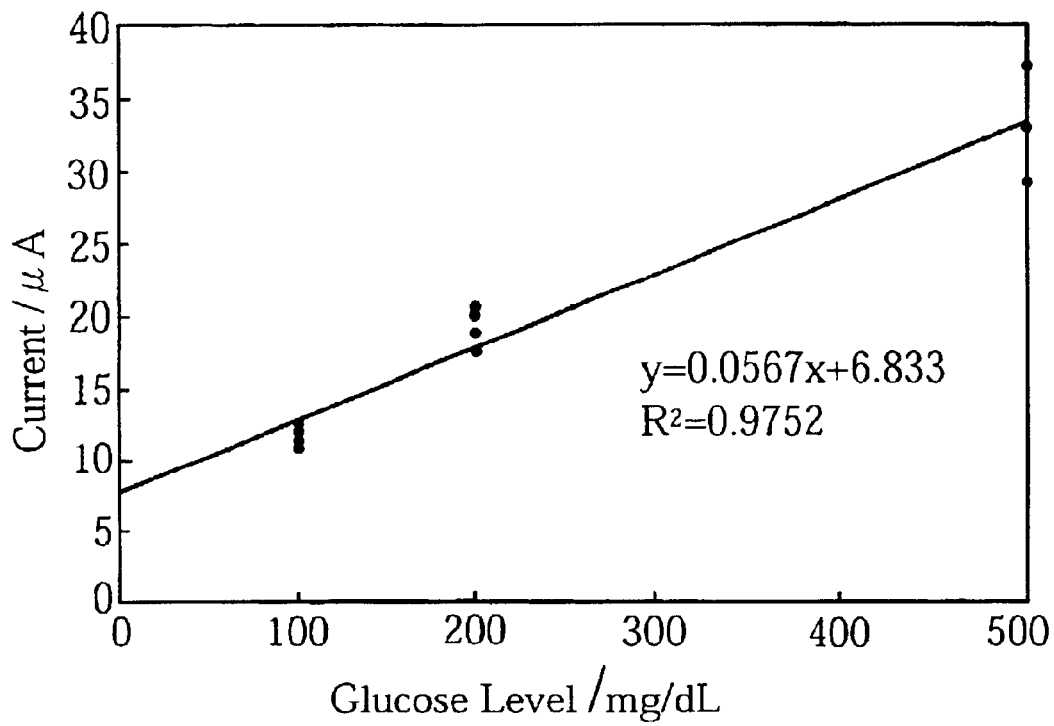
FIG. 8a is a figure illustrating the result of a regression analysis based on the result of measurement shown in FIG. 7.
FIG. 8b is a table illustrating a result of the regression analysis based on the result of measurement shown in FIG. 7.

Data at 800 mV was extracted from the results of measurement shown in FIG. 7 (presented in FIG. 8b) and regression analysis was carried out concerning a relationship between the glucose level and a value of the current generated. As a result, a linear equation expressing a correlation was yielded as shown in FIG. 8a. The linear equation presented in a graph is that linearly approximated by a least-square method on the basis of data shown in FIG. 8b. In FIG. 8a, the linear equation is yielded, as well as an $R^2$ value. As shown in this graph, it can be understood that the value of the current has a tendency to increase linearly according to the glucose level and is measured in a specific rate of change (0.0567) according to the glucose level. Thus, it can be understood that according to the body fluid measuring apparatus according to the present embodiment, the blood glucose level can be accurately measured in practical use.

Figure 9:
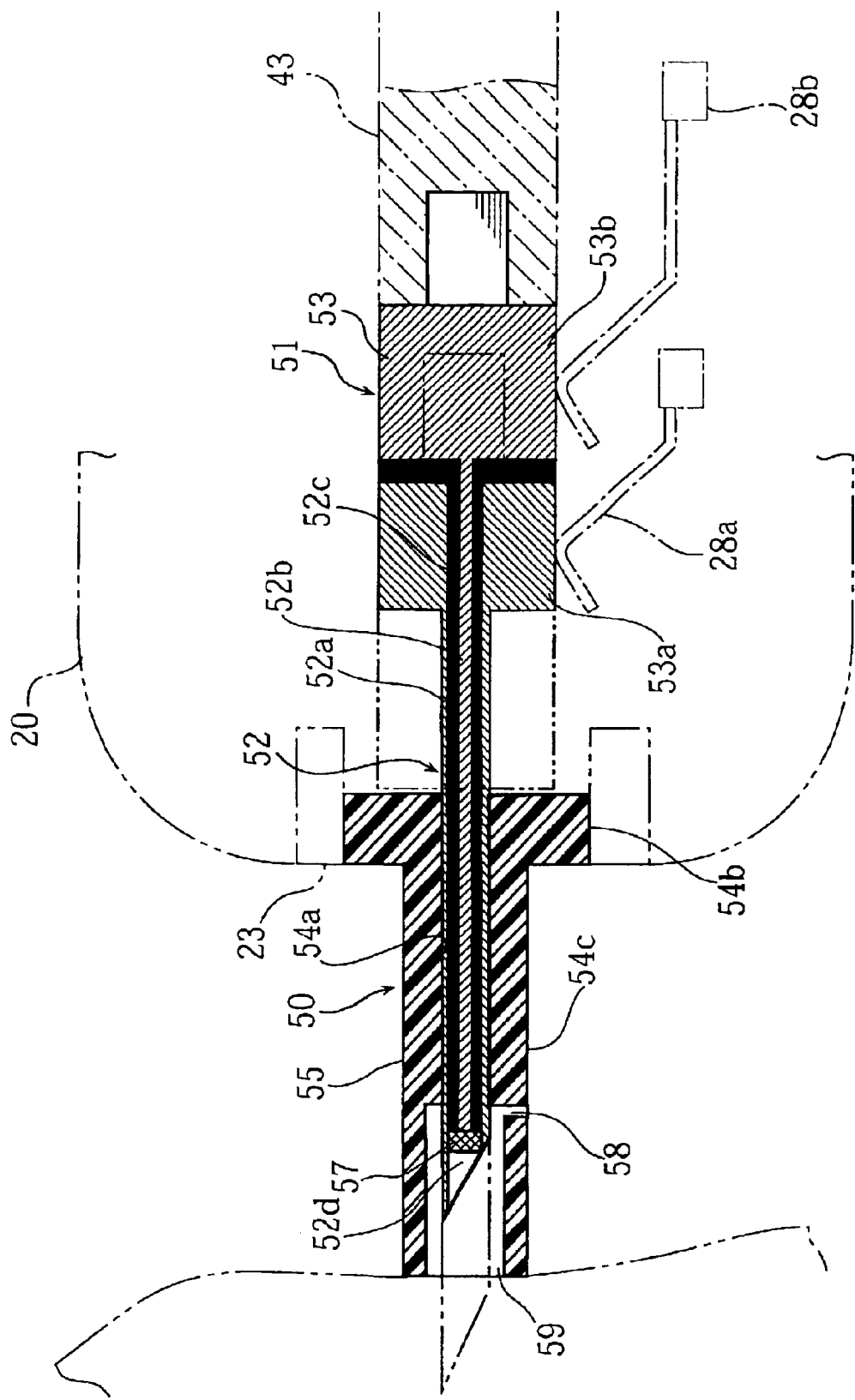
FIG. 9 is an enlarged longitudinal sectional view showing the body fluid sampler of the body fluid measuring apparatus according to the second embodiment of the present invention.

FIG. 9 is an enlarged longitudinal section view showing the body fluid sampler 50 and the position of the body fluid measuring apparatus according to the second embodiment of the present invention. Structural elements that are the same as the above described embodiment have identical reference numerals attached thereto, and their description will be omitted. The apparatus according to the second embodiment is made by mounting the body fluid sampler 50 with a different shape on a main body 20 that is almost identical to the above described embodiment. This body fluid sampler 50 comprises the fixed member 55 and the movable member 51.

The fixed member 55 consists of an insulative material such as a resin and has a through-hole 54a and also has the larger diameter part 54b and the smaller diameter part 54c. Similar to the above described embodiment, the front end of this fixed member 55 has the space 59 for sucking blood and on the wall of the fixed member 55, the air-vent hole 58 is formed to allow communication between the space 59 and the outside.

The movable member 51 has the lancet 52 with a tapering pointed tip and the larger diameter part 53 integrally formed on its base. The lancet 52 has the outer diameter corresponding to the through-hole 54a of the fixed member 55 and can move reciprocatively in the axial direction in the through-hole 54a. The lancet 52 contains the tube 52a and the axial core 52b and these function integrally as the paired electrodes. Through constituting the paired electrodes by the tube 52a and the axial core 52b, the tube 52a and the axial core 52b is insulated by the insulative material 52c. The insulative material 52c used is exemplified by, for example, silicon resin, epoxy resin, or fluorine-based resin. A very small space 52d, in which the reactive layer 57 is prepared containing the reactive reagent necessary for measurement, is formed inside the pointed tip of the lancet 52. In the larger diameter part 53 of the movable member 51, two parts 53a and 53b electrically connected with the tube 52a and the axial core 52b, respectively, are separated through the insulation layer 52c.

As shown in FIG. 9 using a broken line, inside the main body 20, the fixed terminal 28a allowing connection with the tube 52a of the lancet 52 and the fixed terminal 28b allowing connection with the axial core 52b are installed. The fixed terminals 28a and 28b are installed so as to be capable of making sliding contact with the contact portions 53a and 53b of the movable member 51, respectively. Specifically, when the lancet 52 and the movable member 51 are positioned at predetermined sections in motion in the axial direction, each terminal 28a and 28b contacts with a section represented by the contact portions 53a and 53b of the movable member 51. In this way, at the time of using the apparatus, it becomes possible for the axial core 52b of the lancet 52 to act as the active electrode, for example, and the tube 52a to act as the counterpart electrode. Similar to the first embodiment, the electronic circuit (not illustrated) calculates the value measured for the test material included in the blood glucose level on the basis of the current generated at the electrode. The internal structure of the main body 20 of the second embodiment is identical to that of the main body 20 of the first embodiment except for the constitution of the terminal 28a and the terminal 28b, which are described above.

In preparing the movable member 51, as the tube 52a of the lancet 52, a stainless steel-made and a platinum-made hollow needle can be used having a hollow tapered point portion of 0.3 mm outer diameter and 0.18 mm inner diameter (gauge No. 30) or a hollow pointed portion of 0.26 mm outer diameter and 0.13 mm inner diameter (gauge No. 31). In the case where the tube 52a, which meets the gauge No. 30 lancet 52 is adopted as the axial core 52b of the lancet 52, a wire, which has a very thin part, has a 0.15 mm outer diameter at a thinnest portion and is made from carbon fiber, glassy carbon, graphite, or a noncorrosive metal such as platinum, palladium, or gold. This wire is covered with insulative polytetrafluoroethylene resin high in repellency to make the outer diameter about 0.18 mm meeting the inner diameter of the tube 52a. The hollow needle and the wire each have a larger diameter part 53 indicated by reference numerals 53a and 53b on the base ends. After the end of the wire is cut, the reactive layer 57 is formed on a front end face by a similar method to that of the above described first embodiment. After sufficient drying of the reactive layer 57, the wire is inserted into the sharp tip of the hollow needle to leave the very small space 52d for integration with the hollow needle. As a result, the movable member 51 equipped with the lancet 52 is completed. The polytetrafluoroethylene resin constitutes the insulative material 52C in the lancet 52. An ointment containing silicon may be applied to the pointed tip of the lancet 52, to realize a painless feeling by alleviating a stinging sensation at the time of puncturing the skin.

The size of the fixed member 55 and the lancet 52 are not especially restricted, but as exemplified below, setting is possible to make the necessary sample amount very small in comparison with the conventional sample amount. For example, the acute terminal of the lancet 52 is prepared by cutting obliquely for a proper size and the inner diameter of the very small space 52d inside the acute terminal is made 0.18 mm. At this time, in this very small space 52d, blood to be sampled is of an amount allowing contact with the tube 52a and the reactive layer 57 in the tip of the axial core 52b. Consequently, it can be understood that it is not necessary for blood to fill the whole of the body fluid-sucking chamber 59 of the fixed member 55, which allows sampling of a small amount of blood in comparison with the first embodiment.

Therefore, according to the body fluid measuring apparatus of the second embodiment having such a constitution, the necessary sample amount may be very small making the very small space 52d in the sharp tip of the lancet 52 very thin. As is evident from comparison with the first embodiment, a very small sample can be applied to measurement. In conclusion, the depth for puncturing the skin with the sharpened tip of the lancet 52 may be smaller than the conventional apparatus and even the above described example. Consequently, the body fluid measuring apparatus as shown in FIG. 9 is excellent for realizing alleviation of pain.

Similar to the first embodiment, the body fluid sampler 50 of the present embodiment is, in consideration of proper measurement and from the point of view of hygiene, preferably constituted as a disposable member making it possible to use a new one each time.

The range of the present invention is not restricted to the above described individual embodiments. Individual embodiments are described as those for measurement of blood glucose level, but an object of measurement is not restricted to the blood glucose level. In addition, in individual embodiments, the fixed member and the electrode possessed by the fixed member are made in a cylindrical shape. However, it is not always cylindrical, and may be other tube-like shapes keeping a form surrounding the lancet.

What is claimed is:

1. A body fluid measuring apparatus comprising a main body and a body fluid sampler fitted to the main body,
   wherein the body fluid sampler comprises a fixed member fixed to the main body and a movable member guided by the fixed member, the fixed member being formed with a body fluid-sucking chamber open at a tip of the fixed member and a through-hole communicating therewith, the movable member comprising a lancet acting as a first electrode, the movable member being reciprocatively movable for bringing a tip of the lancet into and out of the tip of the fixed member, the body fluid-sucking chamber being provided with a second electrode and a reactive layer containing a reactive reagent necessary for measurement,
   wherein the main body comprises an electronic circuit for providing a measurement on the basis of an electrical signal from the lancet as the first electrode and the second electrode, and a drive mechanism which drives the movable member for causing the tip of the lancet to project from the tip of the fixed member,
   wherein the fixed member comprises a cylindrical electrode acting as the second electrode and an insulator for electrically separating the cylindrical electrode from the lancet, the cylindrical electrode and the lancet being concentrically arranged, and
   wherein a surface of the insulator facing the lancet is hydrophobically treated.

2. The body fluid measuring apparatus according to claim 1, wherein the reactive layer is provided over an entire wall surface defining the fluid-sucking chamber in the cylindrical electrode.

3. The body fluid measuring apparatus according to claim 1, wherein the drive mechanism comprises an automatic drive mechanism for driving the movable member to first cause the tip of the lancet to project from the tip of the fixed member and to subsequently cause the tip of the lancet to retreat from the tip of the fixed member.

4. The body fluid measuring apparatus according to claim 1, wherein the main body has a fixed terminal connected to the electronic circuit, the movable member of the body fluid sampler comprising a contact portion in slidable contact with the fixed terminal for electrically connecting the lancet to the fixed terminal.

5. The body fluid measuring apparatus according to claim 1, wherein the main body has an annular spring terminal for electrically connecting the second electrode to the electronic circuit, the fixed member of the body fluid sampler being detachably fixed to the main body under urging of the annular spring terminal.

6. The body fluid measuring apparatus according to claim 1, wherein the fixed member is provided with an air-vent hole for enabling the fluid-sucking chamber to communicate with an external space.

7. A body fluid measuring apparatus comprising a main body and a body fluid sampler fitted to the main body,
wherein the body fluid sampler comprises a fixed member fixed to the main body and a movable member guided by the fixed member, the fixed member being formed with a through-hole, the movable member comprising a lancet, the movable member being reciprocatively movable for bringing a tip of the lancet into and out of a tip of the fixed member,
wherein the lancet comprises a tube, an axial core inserted therein, and an insulator for electrically separating the tube and the core, the tube serving as a first electrode, the axial core serving as a second electrode, the tip of the lancet being provided with a reactive reagent for measurement, and
wherein the main body comprises an electronic circuit for providing a measurement on the basis of an electrical signal from the tube and the axial core, and a drive mechanism which drives the movable member for causing the tip of the lancet to project from the tip of the fixed member.

8. The body fluid measuring apparatus according to claim 7, wherein the tube projects further tipwise than the axial core and the insulator, the reactive reagent being attached to a tip of the axial core.

9. The body fluid measuring apparatus according to claim 7, wherein the drive mechanism comprises an automatic drive mechanism for driving the movable member to first cause the tip of the lancet to project from the tip of the fixed member and to subsequently cause the tip of the lancet to retreat from the tip of the fixed member.

10. The body fluid measuring apparatus according to claim 7, wherein the main body has first and second fixed terminals connected to the electronic circuit, the movable member comprising a first contact portion in slidable contact with the first fixed terminal for electrically connecting the tube to the first fixed terminal and a second contact portion in slidable contact with the second fixed terminal for electrically connecting the axial core to the second fixed terminal.

11. The body fluid measuring apparatus according to claim 7, wherein the fixed member is provided with an air-vent hole for enabling an internal space of the fixed member to communicate with an external space.

12. A body fluid sampler mounted, in use, on a body fluid measuring apparatus, comprising:
a fixed member and a movable member guided by the fixed member, the fixed member being formed with a body fluid-sucking chamber open at a tip of the fixed member and a through-hole communicating therewith, the movable member comprising a lancet acting as a first electrode, the movable member being reciprocatively movable for bringing a tip of the lancet into and out of the tip of the fixed member, the body fluid-sucking chamber being provided with a second electrode and a reactive layer containing a reactive reagent necessary for measurement,
wherein the fixed member comprises a cylindrical electrode acting as the second electrode and an insulator for electrically separating the cylindrical electrode from the lancet, the cylindrical electrode and the lancet being concentrically arranged, and
wherein a surface of the insulator facing the lancet is hydrophobically treated.

13. The body fluid sampler according to claim 12, wherein the movable member comprises a contact portion for slidable contact with a fixed terminal mounted to a main body of the body fluid measuring apparatus to which the body fluid sampler is attached, the contact portion being held in conduction with the lancet.

14. A body fluid sampler mounted, in use, on a body fluid measuring apparatus, comprising:
a fixed member and a movable member guided by the fixed member, the fixed member being formed with a through-hole, the movable member comprising a lancet, the movable member being reciprocatively movable for bringing a tip of the lancet into and out of a tip of the fixed member,
wherein the lancet comprises a tube, an axial core inserted therein, and an insulator for electrically separating the tube and the core, the tube serving as a first electrode, the axial core serving as a second electrode, the tip of the lancet being provided with a reactive reagent for measurement.

15. The body fluid sampler according to claim 14, wherein the movable member comprises a first contact portion for slidable contact with a first fixed terminal mounted to a main body of the body fluid measuring apparatus to which the body fluid sampler is attached, and a second contact portion held in slidable contact with a second fixed terminal mounted to the main body, the first contact portion being held in conduction with the tube, the second contact portion being held in conduction with the axial core.

16. The body fluid sampler according to claim 14, wherein the tube projects further than the axial core and the insulator, the reactive reagent being attached to a tip of the axial core.

17. A body fluid measuring apparatus comprising a main body and a body fluid sampler fitted to the main body,
wherein the body fluid sampler comprises a fixed member fixed to the main body and a movable member guided by the fixed member, the fixed member being formed with a body fluid-sucking chamber open at a tip of the fixed member and a through-hole communicating therewith, the movable member comprising a lancet acting as a first electrode, the movable member being reciprocatively movable for bringing a tip of the lancet into and out of the tip of the fixed member, the body fluid-sucking chamber being provided with a second electrode and a reactive layer containing a reactive reagent necessary for measurement,
wherein the main body comprises an electronic circuit for providing a measurement on the basis of an electrical signal from the lancet as the first electrode and the second electrode, and a drive mechanism which drives the movable member for causing the tip of the lancet to project from the tip of the fixed member, and wherein the main body has an annular spring terminal for electrically connecting the second electrode to the electronic circuit, the fixed member of the body fluid sampler being detachably fixed to the main body under urging of the annular spring terminal.

18. A body fluid measuring apparatus comprising a main body and a body fluid sampler fitted to the main body, wherein the body fluid sampler comprises a fixed member fixed to the main body and a movable member guided by the fixed member, the fixed member being formed with a body fluid-sucking chamber open at a tip of the fixed member and a through-hole communicating herewith, the movable member comprising a lancet acting as a first electrode, the movable member being reciprocatively movable for bringing a tip of the lancet into Ada out of the tip of the fixed member, the body fluid-sucking chamber being provided with a second electrode and a reactive layer containing a reactive reagent necessary for measurement, wherein the main body comprises an electronic circuit for providing a measurement on the basis of an electrical signal from the lancet as the first electrode and the second electrode, and a drive mechanism which drives the movable member for causing the tip of the lancet to project from the tip of the fixed member, and wherein the fixed member is provided with an air-vent hole for enabling the fluid-sucking chamber to communicate with an external space.

* * * * *